US006985841B2

(12) United States Patent
Barroux

(10) Patent No.: US 6,985,841 B2
(45) Date of Patent: Jan. 10, 2006

(54) MODELLING METHOD ALLOWING TO PREDICT AS A FUNCTION OF TIME THE DETAILED COMPOSITION OF FLUIDS PRODUCED BY AN UNDERGROUND RESERVOIR UNDER PRODUCTION

(75) Inventor: Claire Barroux, Chaville (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 843 days.

(21) Appl. No.: 09/899,105

(22) Filed: Jul. 6, 2001

(65) Prior Publication Data

US 2002/0016703 A1    Feb. 7, 2002

(30) Foreign Application Priority Data

Jul. 10, 2000    (FR) .................................. 00 09008

(51) Int. Cl.
*G06F 17/50*    (2006.01)
(52) U.S. Cl. .............................. 703/10; 702/13; 702/30
(58) Field of Classification Search ................. 702/30, 702/6, 13; 703/2, 10, 30
See application file for complete search history.

(56) References Cited

U.S. PATENT DOCUMENTS

| 5,710,726 A | 1/1998 | Rowney et al. ............... 703/10 |
| 6,101,447 A * | 8/2000 | Poe, Jr. ......................... 702/13 |
| 6,108,608 A * | 8/2000 | Watts, III ..................... 702/30 |

FOREIGN PATENT DOCUMENTS

| FR | 2756044 | 5/1998 |
| FR | 2775094 | 8/1999 |
| WO | 0037898 | 6/2000 |

OTHER PUBLICATIONS

Wang P et al Comparison Of Flash Calculations For Impes compositional Reservoir Simulators, in Situ, Dekker, New York, NY vol. 21, No. 3 Aug. 1997.
Odeh A S "Comparison Of Solutions To A Three-Dimensional Black-Oil Reservoir Simulation Problem" Journal of Petroluem Technology US, AIME Dallas, TX, vol. 33 No. 1, 1981 pp 13-25.
Leibovici et al—A Consistent Procedure For Pseudo-Component Delumping Fluid Phase Equilibria, NL Elsevier Scientific Publishing Company, Amsterdam vol. 117 1996 pp 225-232.

(Continued)

*Primary Examiner*—Thai Phan
(74) *Attorney, Agent, or Firm*—Antonelli, Terry, Stout and Kraus, LLP.

(57) ABSTRACT

Method using <<Black Oil>> type modelling for predicting, as a function of time, the detailed composition of fluids produced by an underground reservoir under production, combined with a delumping stage allowing detailed thermodynamic representation of the reservoir fluids.

The input data entered for the model are the thermodynamic parameters of the fluids such as viscosity, volume factor, density, gas-oil dissolution ratio, etc. (in form of charts, and/or by correlation, as a function of the pressure, of the temperature if it varies) and, if need be, an additional parameter keeping a memory of the composition of the gas such as, for example, the density of the gas), as well as data relative to the variations, as a function of the same <<abscissas>>, of the phase parameters required for delumping, without the latter being used during the <<Black Oil>> simulation of the flows.

Application: predictive profiles of the detailed composition of hydrocarbons produced by a reservoir for example.

5 Claims, 2 Drawing Sheets

OTHER PUBLICATIONS

JA Trangenstein et al "Mathematical Structure Of Compositional Reservoir Simulation "Siam Journal Of Scientific And Statistical Computing US, Phil. PA, vol. 10, No. 5, Sep. 1, 1989 pp 817-845.

* cited by examiner

MODELLING METHOD ALLOWING TO PREDICT AS A FUNCTION OF TIME THE DETAILED COMPOSITION OF FLUIDS PRODUCED BY AN UNDERGROUND RESERVOIR UNDER PRODUCTION

FIELD OF THE INVENTION

The present invention relates to a modelling method allowing to predict, as a function of time, the detailed composition of fluids produced by an underground reservoir under production, and notably a hydrocarbon reservoir under production.

Such a model allows reservoir engineers to establish detailed compositional profiles that are in particular necessary for predictive dimensioning and management of surface installations, such as separators, treating plants, transport lines, etc., and therefore useful in surface and process engineering.

BACKGROUND OF THE INVENTION

Modelling of flows in a petroleum reservoir is essentially based on the application, to the previously gridded reservoir (or to a portion thereof), of the well-known Darcy's law describing the flow of fluids in porous media, of the law of mass conservation in each volume unit, of the thermodynamic relations that govern the evolution of the phase parameters of the fluids such as viscosity, density, on initial conditions, on structural closure boundary conditions and on bottomhole conditions.

The <<Black Oil>> model, referred to as B.O. hereafter, is one of the most commonly used models in petroleum simulation. It allows to describe a compressible three-dimensional and three-phase (water-oil-gas) flow. The petroleum effluents involved in this model are generally described by a water constituent and by two constituents for the reservoir fluid, the term constituent covering here the notion of component (such as $H_2O$ for water) and the notion of pseudo-component (group of components). The constituents involved in this model are three in number: a water constituent (E), a heavy hydrocarbon constituent (L) and a light hydrocarbon constituent (V). In a B.O. type model referred to as <<strict>>, constituent (E) is present only in the water phase, constituent (L) is present only in the liquid hydrocarbon phase (referred to as oil or condensate), and constituent (V) is distributed among the liquid and vapour hydrocarbon phases (phase referred to as gas). Although the use of B.O. models is not recommended in certain condensate gas cases, it is however applicable to a large number of industrial cases.

Another well-known simulation model, referred to as <<compositional>> model, is also used, wherein the hydrocarbon fluids are represented by a larger number of components, at least three, often more. Modelling the flows of these more detailed fluids leads to very long computing times (much longer than those required for B.O. type modelling) as a result of the larger number of constituents, but also because it is often necessary to reduce the size of the grid cells to limit numerical errors and consequently to increase the number of cells.

For practical reasons, the fluids in place are described as consisting of a number of components or pseudo-components that is much smaller than the real number of components, so that the modelling computations can be carried out within a reasonable period of time. A composition reduced to some 5 or 10 pseudo-components is generally sufficient to represent the behaviour of the fluids in the reservoir.

Patent application WO-99/42,937 and the paper by C. Leibovici and J. Barker <<A Method for Delumping the Results of a Compositional Reservoir Simulation>>, SPE 49068, presented at the SPE Annual Technical Conference and Exhibition New Orleans, 27–30Sep. 1998, describe a method for predicting the evolution of the detailed composition in time, from computations carried out in a compositional type simulation of fluids described by a certain reduced number of pseudo-components (principle of <<lumped>> representation obtained by means of a <<lumping>> operation), the number of components being at least three. The method thus allows to predict the results that would have been obtained with a reservoir simulation using a finely detailed model where the fluids are represented by a larger number of components. This operation is well-known to the man skilled in the art as <<delumping>>.

The principle of the prior delumping stage consists in calculating coefficient $\Delta D_0$ and the n coefficients $\Delta D_p$ (i.e. n+1 coefficients, n being the number of parameters of the equation of state) of a known general equation, previously published in a paper by C. F. Leibovici, E. H. Stenby, K. Knudsen, <<A Consistent Procedure for Pseudo-Component Delumping>>, Fluid Phase Equilibria, 1996, 117, 225–232:

$$\text{Ln}(k_i) = \Delta D_0 + \sum_{p=1}^{n} \Delta D_p \Pi_{pi} \tag{1}$$

where the $\Pi_{pi}$, are fixed characterization parameters of constituent i in the equation of state for a given thermodynamic representation, from the equilibrium constants $k_l$ of each constituent of the lumped thermodynamic representation computed during compositional simulation in each grid cell and at each time interval. If $N_{rg}$ is the number of components of the lumped thermodynamic representation, we thus have $N_{rg}$ equations to determine n+1 coefficients. A necessary condition is therefore that $N_{rg}$ is at least equal to n+1. For Peng-Robinsons's two-parameter equation of state, a lumped thermodynamic representation with at least three components is therefore required.

Once coefficient $\Delta D_0$ and the n coefficients $\Delta D_p$ calculated, they are used for calculating the equilibrium constants of the components of the detailed thermodynamic representation ($N_{rd}$ components) by applying Equation (1) to the $N_{rd}$ components with their own fixed characterization parameters in the detailed thermodynamic representation.

By using a) the equilibrium constants thus determined for the detailed thermodynamic representation, b) the flows between each grid cell and in the wells, c) the vapour fraction in each grid cell from the lumped compositional simulation, and d) the global detailed composition in each grid cell and in the injection wells at the beginning of each time interval, the detailed composition of each hydrocarbon phase at the time interval t and the global detailed composition of each cell at the next time interval (t+1) are then estimated in each cell.

One of the advantages of this method is that it is not necessary, in the delumping stage at each time interval, to solve the equation of state, whether for the lumped representation or for the detailed representation, which allows to save computing time. One drawback of the method is that it is not applicable to B.O. type simulations since convenient equations of state have at least two parameters.

Patent application WO-98/5,710,726 describes a method for predicting the evolution of the detailed composition in time from the flow computations carried out in a B.O. type simulation where the hydrocarbon phases are described by only two components (L) and (V). The drawback of this method is that it requires the use of the equation of state of the detailed representation at each time interval, and it is therefore time-consuming during the delumping stage.

SUMMARY OF THE INVENTION

The method according to the invention combines a predictive simulation of the behaviour of the reservoir by means of B.O. type modelling, which is advantageous in that it requires no equation of state, and a delumping stage wherein no solution of an equation of state is required at any time interval.

In B.O. type modelling, the thermodynamic parameters of the fluids (such as viscosity, volume factor, density, gas-oil dissolution ratio, etc.) are entered, among other parameters, in an input data file of the simulator (in form of charts, and/or by correlation, as a function of the pressure, of the temperature if it varies) as well as, if need be (for the extended B.O. type model), an additional parameter keeping a memory of the composition of the gas such as, for example, the density of the gas.

The basic idea here is to simply enter in the input data the (n+1) additional columns or correlations corresponding to differences $\Delta D_p$, for example by including them in a file incidental to the master file used by the simulation. It is also possible to enter 2×(n+1) additional columns or correlations corresponding to parameters $D_p$ of each phase. A practical condition for data to be entered in form of charts is that the functional dependencies introduced are sufficiently continuous.

Computation of the equilibrium constants by the model is thus no longer required.

The simulation method according to the invention allows to predict, as a function of time and in at least one thermodynamic zone, a detailed composition of a fluid produced by a reservoir and, more particularly, a detailed composition of a fluid contained in and produced by an oil reservoir in which one or more production wells are installed.

It is characterized in that it comprises the following stages:

discretizing the reservoir by means of a grid, each grid cell containing one or more phases, including at least one non-aqueous phase;

determining the variation of thermodynamic parameters of the non-aqueous phases necessary for <<Black Oil>> (B.O.) type modelling during stages of a thermodynamic path followed by the fluids in the reservoir (such as, for example, the viscosity of the phases, the gas-oil dissolution ratio, the volume factors of the oil or the compressibility of the gas, etc.);

defining the fluids by a detailed representation with $N_{rd}$ components and/or pseudo-components;

determining at least one equation of state with n parameters allowing to simulate, at least during the input data preparation stage (a simulation that is strictly necessary only during this input data preparation stage, and therefore not repetitively necessary during or after the B.O. type simulation), the thermodynamic behaviour of the fluids during the stages of a thermodynamic path, allowing to generate, per thermodynamic range or zone, n+1 additional functional relations (in form of charts or of correlations);

converting the thermodynamic behaviour of each non-aqueous phase into input data suited for a B.O. type thermodynamic representation, this input data being completed by the additional input data suited for the delumping operation;

carrying out B.O. type modelling, which allows to determine, in each grid cell and at successive time intervals, thermodynamic characteristics of each non-aqueous phase and data representative of phase displacements in the reservoir; and carrying out a delumping operation in order to obtain the detailed composition of the fluids in each cell.

In order to characterize the thermodynamic path, the variations in the composition of the fluids and in the properties of the various phases are for example determined.

During B.O. type simulation, thermodynamic parameters are for example determined in each cell, such as pressure ($p_j^m$), temperature $T_j^m$ if it varies, the saturations of the liquid ($So_j^m$) and vapour $Sg_j^m$) hydrocarbon phases, the injection or production rates, and, for each pair of cells (j,h), the volume flow rates of the liquid $u_{ojh}^m$) and vapour $u_{gjh}^m$) phases.

The delumping operation comprises for example determining the equilibrium constants from input data specific to the delumping operation, and converting results expressed in volume into results that can be used in molar or mass quantities conservation equations.

BRIEF DESCRIPTION OF THE FIGURES

Other features and advantages of the method according to the invention will be clear from reading the description hereafter, given by way of non limitative example, with reference to the accompanying drawings wherein.

DETAILED DESCRIPTION

Figure 1:
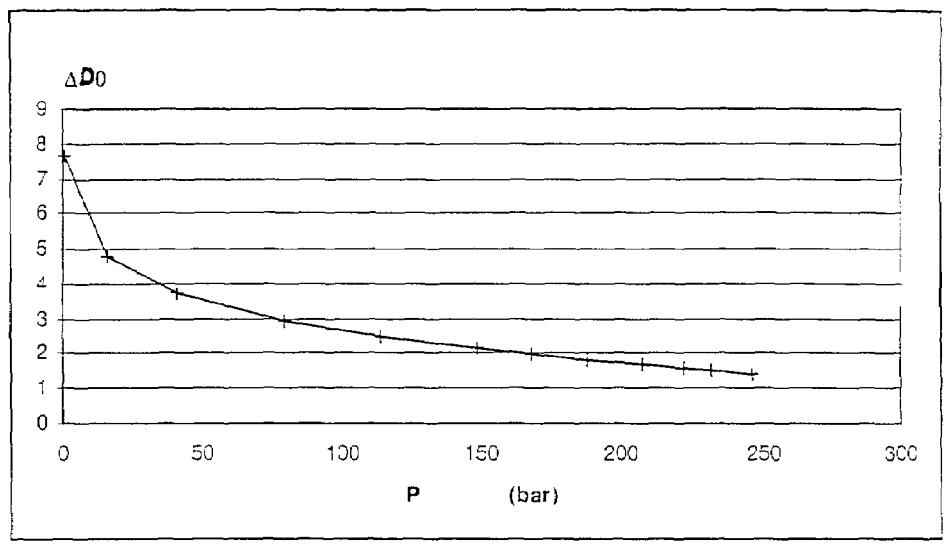
FIGS. 1 to 3 respectively show the variations, as a function of pressure, of three coefficients $\Delta D_0$, $\Delta D_1$, $\Delta D_2$ during the differential vaporization of a reservoir oil simulated by means of Peng-Robinson's two-parameter equation.

The various stages of the modelling method allowing notably to predict, as a function of time, the detailed composition of fluids produced by a hydrocarbon reservoir under production are as follows:

a) The reservoir is first represented in form of a network of grid cells (j), each cell forming an elementary volume filled with fluid(s) in form of one or more phases, with at least one non-aqueous phase. The non-aqueous phases are referred to as hydrocarbon phases although they can contain certain components other than hydrocarbons, such as nitrogen, carbon dioxide, sulfur dioxide.

b) The thermodynamic behaviour of the non-aqueous phase(s) required for a B.O. type thermodynamic representation is established in a way known in the art. The purpose is to describe the dependence of phase parameters on the pressure, the temperature if it varies during simulation, and possibly, for non-strict B.O. type modelling, an indicator of the evolution of the composition (for example the content of condensate dissolved in the gas phase) during a thermodynamic path (evolution) representative of the path that will be followed by the fluid in the reservoir. The commonest thermodynamic path is that of the differential operation during which the pressure of the mixture is progressively lowered at constant temperature: below the saturation point, one of the phases is removed at each pressure stage (for the differential vaporization of a liquid phase, the gas phase is removed); during this operation, the compositions and the properties of the phases (viscosities, densities, volume factor, gas-oil dissolution ratio in the liquid phase, etc.) are determined.

It can be noted that it is also possible to deal with cases that require the use of several Black Oil thermodynamic representations for example, if the composition at the beginning of the simulation varies with the depth or laterally within the reservoir, or if several local thermodynamic paths can be distinguished during modelling. Several zones or ranges of variation of the thermodynamic or compositional quantities, often referred to as thermodynamic zones by specialists, can thus be defined and used.

The origin of the data relative to the behaviour of the reservoir fluid can be of experimental nature (laboratory experiments), it can result from measurements in the field, or predicted from raw data and from complementary hypotheses by numerically simulating the behaviour of the reservoir fluid. Examples of the phase properties thus usually described as input data for B.O. type modelling are the viscosity of the phases, the gas-oil dissolution ratio, the volume factor of the oil, the compressibility factor of the gas.

c) The fluid is defined, prior to B.O. simulation and for each thermodynamic zone or range, by a detailed representation with $N_{rd}$ components and/or pseudo-components.

d) For each thermodynamic zone, an equation of state allowing to first reproduce, prior to B.O. simulation, the thermodynamic behaviour of the fluid during the thermodynamic path representative of the path that will be followed by the fluid in the reservoir is determined.

e) The stages (often pressure stages) of the thermodynamic path of each zone are reproduced with the equation of state, in particular below the saturation pressure where two phases are present. This prior thermodynamic simulation uses, at the saturation pressure of the fluid and below, at each stage of the thermodynamic path, the equilibrium constants obtained from the simulation results in order to calculate coefficient $\Delta D_0$ and the n coefficients $\Delta D_p$ of Equation (1) corresponding to the equation of state selected to describe the behaviour of the hydrocarbon fluid for example by minimizing the function:

$$O(\Delta D_0, \Delta D_1, \ldots, \Delta D_p, \ldots, \Delta D_n) = \sum_{i=1}^{Nrd}\left[\Delta D_0 + \sum_{p=1}^{n}\Delta D_p \Pi_{pi} - \mathrm{Ln}(k_i)\right]^2 \quad (2)$$

Equation (1) being obtained from an equation on the fugacity of constituent i in a phase where coefficients $D_0$ and the n coefficients $D_p$ specific to the phase appear:

$$\mathrm{Ln}\left(\frac{f_i}{x_i P}\right) = D_0 + \sum_{p=1}^{n} D_p \Pi_{pi}, \quad (3)$$

It is possible to alternately determine these coefficients that appear as phase parameters, the drawback being that the volume of input data is increased.

We thus have, at each stage of the thermodynamic path considered to be representative of the path that will be followed by the fluid in the reservoir, the dependence as a function of the pressure, of the temperature, and possibly other necessary indicators, the properties of the phases necessary for B.O. simulation and, below the saturation pressure, coefficient $\Delta D_0$ and the n coefficients $\Delta D_p$ (or the n+1 parameters $D_0$ and $D_p$, p ranging from 1 to n, by phase) that will be used to calculate the equilibrium constants during the delumping stage described hereafter.

Figure 2:
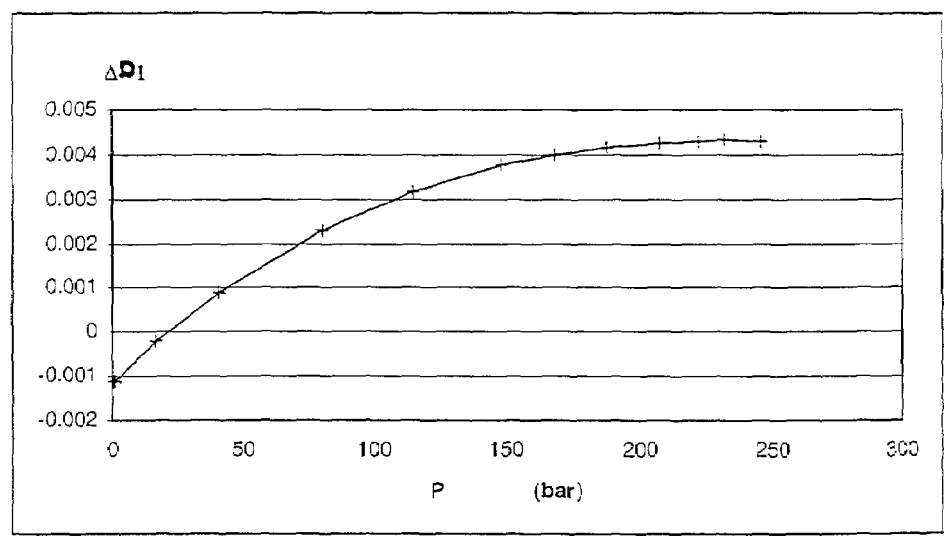
Figure 3:
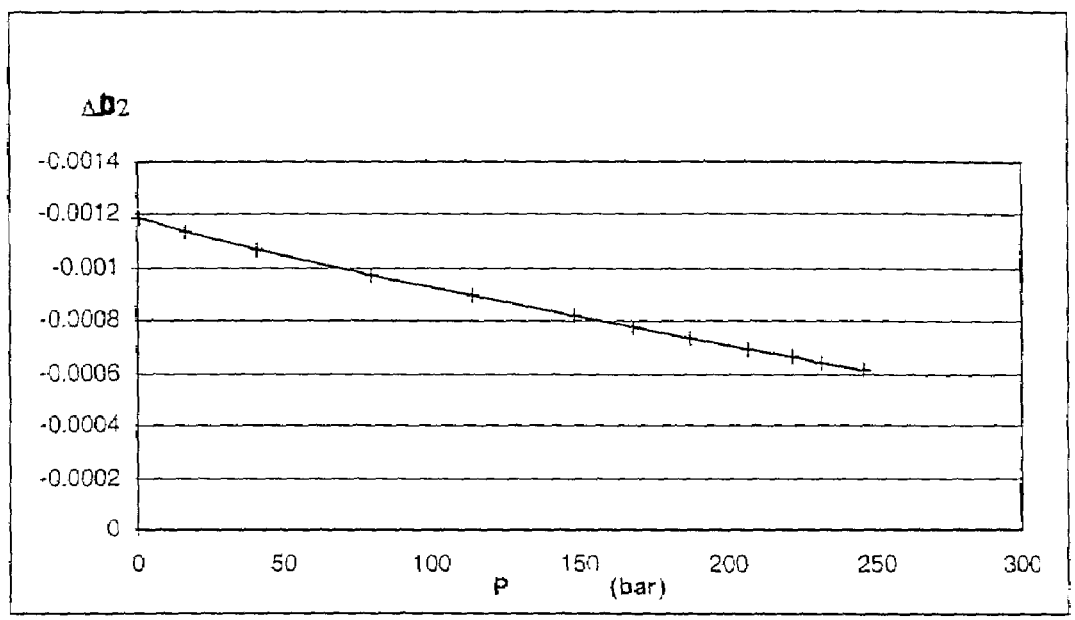

The variations of differences $\Delta D_p$ (p=0 to 2) for a differential operation on a reservoir oil simulated by means of Peng-Robinson's two-parameter equation are illustrated in FIGS. 1 to 3. It can be seen that the behaviour of these parameters is sufficiently continuous to be readily introduced in form of a chart, or by a simple correlation as a function of the pressure. For example, in the present case for $\Delta D_0$:

$$\Delta D_0 = 1{,}406231(1 - LN(P/P\mathrm{sat})[1 + 0{,}038 \times LN(P/P\mathrm{sat})]).$$

It can be convenient to add to the data stored for later use relative to the evolution of the values of these coefficients as a function of the pressure, temperature and compositional indicator abscissas, the evolution of the values of the oil density in the thermodynamic conditions of each stage of the thermodynamic path followed, above as well as below the saturation pressure. It is also possible to store, in addition to or instead of this data, other parameters of the oil and/or gas phases, but this is not essential.

f) The thermodynamic behaviour of the hydrocarbon phase(s) is transposed, in a way known in the art, into one or more B.O. type thermodynamic representation(s) in the input data of the model. These dependences are described above the saturation pressure of the mixture of hydrocarbons and below the saturation pressure, either point by point in charts with an interpolation method and, if need be, an extrapolation method, or by analytical correlations, or by a combination of charts and correlations.

g) A B.O. type simulation is carried out in a way known in the art, said simulation allowing to compute at least in each grid cell (j) and at successive time intervals (m, m+1, etc.), pressure ($p_j^m$), temperature ($T_j^m$) (if it varies), the liquid ($SO_j^m$) and vapour ($Sg_j^m$) hydrocarbon phase saturations, the injection or production rates, and, for each pair of cells (j,h), the volume flow rates of the liquid ($u_{ojh}^m$) and vapour ($u_{gjh}^m$) phases.

h) The equilibrium constants ($k_{ij}^m$) of component i are determined, at each time interval (m) and in each cell (j), from the dependences of coefficients ($\Delta D_0$, $\Delta D_1$, . . . , $\Delta D_p$, . . . , $\Delta D_n$) of Equation (1), or of coefficients ($D_0$, $D_1$, . . . , $D_p$, . . . , $D_n$) of Equation (3) by phase, established at e) with pressure ($p_j^m$), temperature ($T_j^m$) and, if need be with non-strict B.O. modelling, with a composition indicator such as the content of condensate dissolved in the gas phase.

i) The vaporized fraction ($\theta_j^m$) is determined at each time interval (m), in each cell (j), either from the B.O. type simulation results, or, for higher accuracy in case of coexistence of the oil and gas phases, by solving Rachford-Rice's equation known to specialists, which is applied for example in the following document:

Rachford H. H. Jr and Rice J. D.; <<Procedure for Use of Electronic Digital Computers in Calculating Flash Vaporization Hydrocarbon Equilibrium>>, J. Pet. Technol., 1952, 14, 19, from the molar fractions of each component i in the global detailed composition ($z_{ij}^m$) of the hydrocarbon fluid in cell (j) at time interval (m)

$$\sum_{i=1}^{Nrd} \frac{z_{ij}^m (k_{ij}^m - 1)}{1 + (k_{ij}^m - 1)\theta_j^m} = 0. \quad (4)$$

j) The detailed composition of each hydrocarbon phase is estimated at each time interval (m) and in each cell (j) by means of the following relations:

$$x_{ij}^m = \frac{z_{ij}^m (k_{ij}^m - 1)}{1 + (k_{ij}^m - 1)\theta_j^m} \text{ for the oil phase} \quad (5)$$

$$y_{ij}^m = \frac{k_{ij}^m z_{ij}^m (k_{ij}^m - 1)}{1 + (k_{ij}^m - 1)\theta_j^m} \text{ for the gas phase} \quad (6)$$

k) The molar density of the oil phase $\xi o_j^m$ is estimated in cell (j) at time interval (m) for example from the density of the oil $\rho o_j^m$, in cell (j) at time interval (m), from the following relation:

$$\xi o_j^m = \frac{\rho o_j^m}{MMo} \quad (7)$$

MMo being the molar mass of the liquid hydrocarbon phase (referred to as <<oil>>).

In Equation (7), density $\rho o_j^m$ can therefore be obtained from the results, at time interval (m), of the B.O. simulation or from the input data specific to the delumping stage and stored during the prior thermodynamic simulation. MMo can be calculated from the results of the B.O. simulation if the molar mass of the heavy hydrocarbon constituent is defined by default or in the user input data, or from:

$$MMo_j^m = \sum_{i=1}^{Nrd} MM_i x_{ij}^m \quad (8)$$

$MM_i$ being the molar mass of component or pseudo-component i, and quantities $x_{ij}^m$ being calculated in the previous stage.

l) The molar density of the gas phase $\xi g_j^m$ is estimated in each cell (j) at each time interval (m), either from input data specific to the delumping stage and stored during the prior thermodynamic simulation, or from the results of the B.O. simulation at pressure $P_j^m$, temperature $T_j^m$, for example, when the compressibility factor of the gas is included in the input data of the B.O. type thermodynamic representation, with the following relation:

$$\xi g_j^m = \frac{P_j^m}{Z g_j^m R T_j^m} \quad (9)$$

$Zg_j^m$ being the compressibility factor of the gas, R the perfect gas constant, or, for example, if it is the volume factor of the gas that is included in the input data of the B.O. type thermodynamic representation, with the following relation:

$$\xi g_j^m = \frac{1}{Bg_j^m Vmolst} \quad (10)$$

Vmolst being the molar volume of the gas under standard conditions and $Bg_j^m$ being the volume factor of the gas.

m) The molar flow rates of the liquid ($u_{ojh}^m$) and vapour ($u_{gjh}^m$) phases are evaluated in each cell (j) at each time interval (m) from the volume flow rates of the liquid ($u_{ojh}^m$) and vapour ($u_{gjh}^m$) phases obtained during B.O. simulation and the molar densities obtained in stages k) and l).

n) The molar fraction of each component or pseudo-component i is estimated at time interval m+1 in the global detailed composition ($z_{ij}^{m+1}$) of the hydrocarbon fluid in cell (j), knowing the molar fraction ($z_{ij}^m$) at time interval m, from the following equations:

$$z_{ij}^{m+1} = \frac{z_{ij}^m N_j^m - \Delta t (y_{ij}^m S_{gj}^m + x_{ij}^m S_{oj}^m) - \Delta t \sum_{h \in J(j)} (y_{ij}^m u_{gjh}^m + x_{ij}^m u_{ojh}^m)}{N_j^{m+1}} \quad (11)$$

$$N_j^{m+1} = N_j^m - \Delta t (S_{gj}^m + S_{oj}^m) - \Delta t \sum_{h \in J(j)} (u_{gjh}^m + u_{ojh}^m) \quad (12)$$

Equation (12) expressing the total hydrocarbon molar balance on cell (j), $N_j^m$ being the hydrocarbon molar amount contained in cell (j) at time interval (m), taking into account the matter exchanges with all the cells (h) adjoining (j) which form set J(j).

In Equation (11), the writing of terms ($y_{ij'}^m$) and ($x_{ij'}^m$) —wherein j'=j for a flow from cell (j) to cell (h) or in the well, and j'=h for a flow from cell (h) to cell (j), j' corresponding to the fluid injected in the case of injection wells, S being then negative—implicitly presupposes the use of a simple upstream pattern for the compositional flows. A more general writing of these terms is ($y_{ijh}^m$) and ($x_{ijh}^m$), where $x_{ijh}^m$ and $y_{ijh}^m$ describe the compositions of the liquid and gas phases, obtained in a way known in the art, flowing between cells (j) and (h).

Source terms (molar flow rates) ($S_{gj}^m$) and ($S_{oj}^m$) are obtained from source terms (volume flow rates) ($S_{gj}^m$) and ($S_{oj}^m$) in the B.O. simulation by repeating stages j) to m) for the source terms.

Stages h) to n) describe the delumping operation. The details provided are based on equations of conservation in moles; they could just as well be based on equations of conservation in mass.

From the moment that one knows how to describe the detailed composition in each cell of the B.O. type simulation model at the time t, which can be, in particular, the initial time, one can describe, by means of the present method, the evolution of the detailed composition in each cell during the development process modelled in a <<Black Oil>> type model.

What is claimed is:

1. A modelling method allowing to predict, as a function of time, the detailed composition of fluids produced by an underground reservoir under production, in at least one thermodynamic zone defined in the model, characterized in that it comprises:

discretizing the reservoir by means of a grid, each grid cell containing one or more phases, including at least one non-aqueous phase;

determining the variation of thermodynamic parameters of the non-aqueous phases necessary for <<Black Oil>> (B.O.) type modelling during stages of a thermodynamic path followed by the fluids in the reservoir;

defining the fluids by a detailed representation with $N_{rd}$ components and/or pseudo-components;

determining at least one state function with n parameters allowing to simulate, at least in the input data preparation stage, the thermodynamic behaviour of the fluids during the stages of the thermodynamic path followed, so as to generate, in each said thermodynamic zone where it is desired to perform a delumping operation, additional input data;

converting the thermodynamic behaviour of each non-aqueous phase into input data suited for a B.O. type thermodynamic representation, this input data being completed by said additional input data suited for a delumping operation;

carrying out B.O. type modelling allowing to determine, in each cell and at successive time intervals, thermodynamic characteristics of each non-aqueous phase and data representative of phase displacements in the reservoir; and carrying out a delumping operation in order to obtain the detailed composition of the fluids in each cell.

2. A method as claimed in claim 1, characterized in that the thermodynamic path is characterized by determining the variations in the composition of the fluids and the properties of the various phases.

3. A method as claimed in claim 1, characterized in that thermodynamic parameters such as pressure ($p_j^m$), temperature ($T_j^m$), if it varies, the saturations of the liquid ($So_j^m$) and vapour ($Sg_j^m$) hydrocarbon phases, the injection or production rates, and, for each pair of cells (j,h), the volume flow rates of the liquid ($u_{ojh}^m$) and vapour ($u_{gjh}^m$) phases, are determined in each cell during B.O. type simulation.

4. A method as claimed in claim 1, characterized in that the delumping operation comprises determining equilibrium constants from input data specific to the delumping operation, and converting results expressed in volume into results that can be used in molar or mass quantities conservation equations.

5. A method as claimed in claim 1, characterized in that each state function is used to generate n+1 additional functional relations in form of data charts or of correlations, that are included in the input data.

* * * * *